United States Patent [19]

Newman et al.

[11] Patent Number: 5,430,015
[45] Date of Patent: Jul. 4, 1995

[54] ACYLATION OF TETRALINS

[75] Inventors: Christopher P. Newman, Canterbury; Karen J. Rossiter; Terence L. Miller, both of Ashford, all of Great Britain

[73] Assignee: Unilever Patent Holdings, BV, Vlaardengen, Netherlands

[21] Appl. No.: 32,046

[22] Filed: Mar. 16, 1993

[30] Foreign Application Priority Data

Mar. 16, 1992 [EP] European Pat. Off. ............ 92302237

[51] Int. Cl.$^6$ ................................................ A61K 7/46
[52] U.S. Cl. ...................................... 512/17; 568/319; 568/323; 568/328; 585/459
[58] Field of Search .................. 568/319, 323; 512/17; 585/459

[56] References Cited

U.S. PATENT DOCUMENTS

| | | | |
|---|---|---|---|
| 3,509,215 | 4/1970 | Wood et al. | 512/17 |
| 4,162,256 | 7/1979 | Sprecker et al. | 512/17 |
| 4,178,311 | 12/1979 | Specker et al. | 568/703 |
| 4,352,748 | 10/1982 | Traas et al. | 512/17 |
| 4,466,908 | 8/1984 | Specker et al. | 512/17 |
| 4,551,573 | 11/1985 | Cobb | 585/459 |
| 5,087,720 | 2/1992 | Frank | 512/17 |

FOREIGN PATENT DOCUMENTS

| | | | |
|---|---|---|---|
| 1393449 | 2/1965 | France | 512/17 |
| 58-35142 | 3/1983 | Japan | 512/17 |
| 410926 | 4/1966 | Netherlands | 568/703 |

*Primary Examiner*—James H. Reamer
*Attorney, Agent, or Firm*—Cushman, Darby & Cushman

[57] ABSTRACT

A method of acetylating 1,2,3,4,-tetrahydro-1,1,2,4,4,7-hexamethylnapthalene (HMT) to produce 6-acetyl-1,2,3,4-tetrahydro-1,1,2,4,4,7-hexamethlnaphthalene (acetyl-HMT), comprises subjecting a mixture of 1,2,3,4-tetrahydro-1,1,2,4,4,7-hexamethlnaphthalene and or one or more substituted indanes or substituted acetylindanes to a Friedel-Crafts acetylation reaction in the presence of a saturated hydrocarbon solvent.

17 Claims, 1 Drawing Sheet

ACYLATION OF TETRALINS

FIELD OF INVENTION

This invention concerns the acylation of tetralins, particularly hexamethyltetralin (HMT).

BACKGROUND OF THE INVENTION

Acetylated tetralins and indanes are important musk fragrances widely used in the fragrance industry. Very well known among them is the acetylated tetralin 6-acetyl-1,2,3,4-tetrahydro-1,1,2,4,4,7-hexamethylnapthalene (the structure of which is shown in FIG. 1), which is also known by the trade names Tonalide, Tetralide and Fixolide. This musk can be prepared by acetylation of the corresponding tetrahydronaphthalene 1,2,3,4-tetrahydro-1,1,2,4,4,7-hexamethylnaphthalene which is sometimes also referred to as 1,1,3,4,4,6-hexamethyltetralin (and which is referred to herein as "HMT" for brevity), by the reaction shown in FIG. 2. The musk is thus referred to herein as "acetyl-HMT" for brevity.

Chlorinated solvents are conventionally used in such processes, but these are now considered environmentally undesirable. The present applicants have attempted to produce acetyl-HMT by acetylation of HMT using more environmentally acceptable saturated hydrocarbon solvents, particularly cyclohexane or other alicyclic solvents. However, they found that although this is possible on a small laboratory scale, it was difficult in practice on a larger scale, because a complex between the Lewis acid used and the ketonic product was formed which is insoluble or difficultly soluble in the non-halogenated solvent, with the consequence that the whole mixture is very difficult to stir or may even set solid. In large scale reaction vessels this may lead to an uneven temperature distribution and local overheating in the reaction mixture, and even damage to the stirring equipment. Also, the reaction vessel cannot or only with difficulty be emptied. Attempts to maintain the reaction mixture in liquid state by heating lead to unsatisfactory results due to poorer selectivity (either by side reaction, or by further reaction of the product), loss of volatile materials and unpredictable resolidification. Nevertheless, to prevent the difficulties caused by solidification of the reaction mixture, it is important that the reaction mixture either remains mobile at the reaction temperature or may be maintained in a mobile state by a moderate rise in temperature, preferably near or after completion of the addition of all components of the reaction mixture.

It has now been found that by performing an acylation reaction on a mixture of HMT and one or more substituted indanes and/or substituted acylindanes, it is possible successfully to perform the acylation reaction using a non-halogenated saturated hydrocarbon solvent, and so to produce acyl-HMT in a more environmentally acceptable way than has hitherto been feasible in practice.

Statement of the invention

Thus, in one aspect the present invention provides a method of acylating 1,2,3,4,-tetrahydro-1,1,2,4,4,7-hexamethyl-naphthalene (HMT) to produce 6-acyl-1,2,3,4-tetrahydro-1,1,2,4,4,7-hexamethylnaphthalene (acyl-HMT), comprising subjecting a mixture of 1,2,3,4-tetrahydro-1,1,2,4,4,7-hexamethylnaphthalene and one or more substituted indanes and/or substituted acylindanes to a Friedel-Crafts acylation reaction in the presence of a saturated hydrocarbon solvent.

Althought the method can be used advantageously to produce other acyl-tetralins from HMT besides acetyl-HMT, by choosing the proper acylation reagent, the acetyl-HMT is the most important compound and its preparation will be used to further outline the method according to the invention.

It is not fully understood why inclusion of a substituted indane or acylindane makes the procedure possible: it is thought in some way this might prevent undesirable precipitation of the acetyl-HMT: $AlCl_3$ complex, possibly by acting to inhibit crystal formation and/or growth.

HMT reacts to produce acetyl-HMT in the usual way, and indane(s) reacts to produce the corresponding acetylindane, which can itself be a musk, depending on the type of indane. The process of the invention can thus result in production of a mixture of acetylated hydrocarbons which is commercially useful without it being necessary to separate the acetyl-HMT from all indanes for further use.

The general acetylation reaction of an indane to the corresponding acetylindane is shown in FIG. 3. For use in the present invention, the indane may include a variety of substituents at different positions. It is preferred to use substituted indanes having up to 20 carbon atoms (or the corresponding acetylindanes), and it is found that higher molecular weight indanes generally have a greater effect. Substituted indanes including the following have given good results in the process of the invention:

1-isopropyl-1,3,3,6-tetramethylindane; for brevity this particular substituted indane is referred to herein as "ITMI";

1-(4-methylphenyl)-1,3,3,6-tetramethylindane; for brevity this particular substituted indane is referred to herein to as "MPTMI";

1,1,2,3,3,6-hexamethylindane;
1-ethyl-1,3,3,6-tetramethylindane;
1-isopropyl-2,3,3,5-tetramethylindane.

It is also possible additionally or alternatively to include an acetylindane, for example recycled from the acetylation of the substituted indane initially present.

It is found advantageous to include at least a small amount of MPTMI.

HMT is preferably present in an amount of about 60 to 85% by weight, more preferably 60–80%, with the remainder being mainly substituted indane(s) (or acetylindane(s)). Good results have been obtained with a mixture of ITMI and MPTMI, together constituting between 15 and 40% by weight, preferably between 20 and 40% by weight, of the total reaction mixture. Acceptable results from a point of view of acetyl-HMT yield (on HMT used) have also been obtained using mixtures containing less than 60% HMT, however, since acetyl-HMT is the most important compound from a commercial point of view, reaction mixtures containing less than 60% acetyl-HMT are clearly less commercially useful. The ITMI is preferably present in an amount in a range 0 to 40% by weight, and the MPTMI in an amount in a range 0 to 20% by weight. Suitable reaction mixtures are as follows:

HMT 65–80% particularly 70–75% by weight
ITMI 10–25%, particularly 15–20% by weight
MPTMI 2–25%, particularly 5–20% by weight Such a mixture is conveniently obtained by Friedel-Crafts alkylation of p-cymen-8-ol with a suitable alkene, as described in EP 0 393 742 and U.S. Pat. No. 5,079,386, to give HMT, with MPTMI and ITMI present as byproducts, for example as described below. The product of this reaction, hereinafter referred to as "crude", can be used in the process of the present invention without requiring separation of the indanes and tetralins produced and is found to give good results.

The hydrocarbon solvent is aliphatic preferably alicyclic, with preferred solvents being cyclohexane, methylcyclohexane and trans-decalin.

The method can be carried out using solvent ratios of 10:1 (weight of solvent: weight of HMT+indanes) or lower, e.g. 5:1 (i.e. similar to ratios conventionally used for chlorinated solvents) or lower still, and good results have been obtained at solvent ratios of typically 1:1 or even lower.

The invention can be carried out using any suitable Lewis acid catalyst, for example titanium or aluminium halogenides, preferably aluminium chloride. Preferably more than 50 mole percent of Lewis acid based on HMT (+ indane, as the case may be) is used, more preferably at least 60%, but at least 100 mole percent is needed to get substantially complete conversion of HMT in one reaction run.

The acetylation reaction can be carried out using acetic acid anhydride or acetyl halogenide and is conveniently carried out using acetyl chloride to give the acetyl derivatives. The acetylating reagent is conveniently present in up to 20% molar excess, preferably 10–20%.

The order of steps in the acetylation reaction is not critical. It is currently preferred initially to mix the HMT, substituted indane (or acetylindane), solvent and acetyl chloride, and then to add the Lewis acid catalyst gradually over a period of time. Alternatively, the solvent, acetyl chloride and Lewis acid catalyst can be initially mixed, and the HMT/substituted indane (and-/or acetylindane) mixture added to that mixture over a period of time.

Desirably the reaction is carried out initially at temperatures below about 40° C., more preferably below about 25° C., and good results have been obtained at reaction temperatures of about 10° C. By performing the reaction, at relatively low temperatures, fewer unwanted side reactions occur than would otherwise be the case. By suitable choice of reactants it is possible for the acetylation reaction to be performed without solidification occurring. This may require slightly raising the temperature when the addition of all reaction components is completed or almost completed; in other cases the reactants may solidify but can easily be made mobile again by moderate heating. Nevertheless the temperature should preferably not exceed 40° C. until the reaction is substantially completed.

The reaction mixture is worked up in the usual way and the crude product separated from unwanted by-products as known in the art, particularly by distillation. The Acetyl-HMT may be separated from acetylated indanes to any desired degree, but, as already mentioned above, the acetylation products of certain indanes which are useful in the method of the invention are known in the art to be musk fragrances and thus may remain in the product without detractiong from its usefulness in perfumery.

The invention also includes within its scope the product of the method. Thus, in a further aspect the invention provides a composition of matter comprising a mixture of 6-acetyl-1,2,3,4-tetrahydro-1,1,2,4,4,7-hexamethylnaphthalene in an amount in the range of 60 to 90%, preferably 60–85% by weight, more preferably 75 to 85%, and acetylindane(s) in an amount in the range of 10 to 40% by weight, preferably 15 to 40%, more preferably 15–25%.

Finally, the product of the method can be used in the fragrance industry as is known in the art for conventional acetylated tetralines and indanes. Thus, the invention includes within its scope fragrance mixtures, conventionally known in the art as "perfumes", comprising the product of the method.

The invention will be further described, by way of illustration, in the following Examples and by reference to the accompanying Figures, in which.

Figure 1:
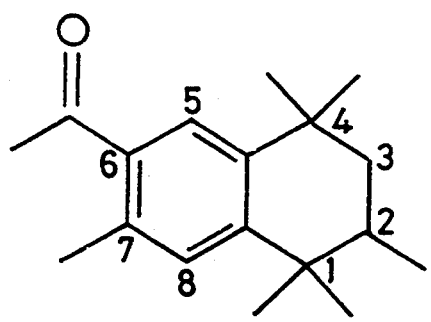
FIG. 1 shows the structure of acetyl-HMT.
Figure 2:
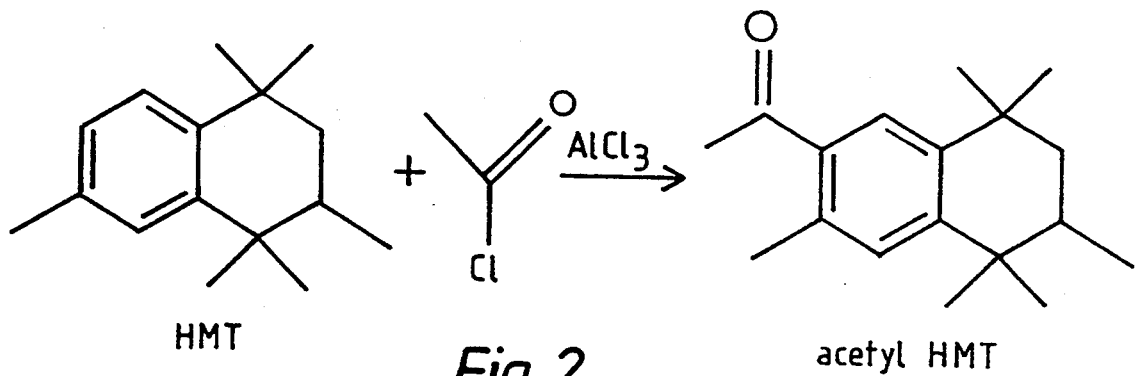
FIG. 2 shows the acetylation reaction of HMT to produce acetyl-HMT.
Figure 3:
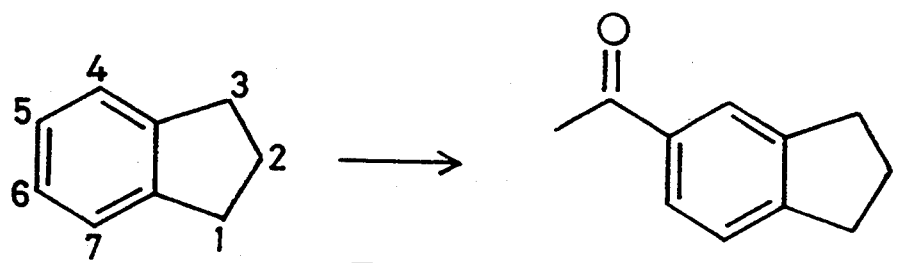
FIG. 3 shows the acetylation reaction of an indane to produce the corresponding acetylindane.

The Examples illustrate use of a range of different substrates, different solvents and different reaction conditions, as follows:

Examples 1–1f use pure HMT substrate. They show the unpredictable solidification of the reaction mixture and the sometimes substantial rise in temperature needed to remobilize the reaction mixture again.

Examples 2–7 use crude HMT substrate, with lower reaction temperature in Example 3 and different solvents in Examples 4 to 7. They show that the presence of ITMI and MPTMI, obtained as byproducts in the synthesis of HMT from cymenol, cause the reaction mixture to remain mobile during the acetylation reaction.

Examples 8–21 use substrates comprising mixtures of HMT with various substituted indanes, particularly HMT and ITMI (Examples 8–14) and HMT and MPTMI (Examples 7–21). They show that the presence of one or more of these compounds keeps the reaction mixture mobile until very near completion of the addition of the AlCl$_3$ and furthermore that only a slight rise in temperature is needed make the mixture mobile again.

Examples 22–24 use ternary substrates comprising mixtures of HMT, ITMI and MPTMI and show the advantages thereof as in Examples 2–7.

Examples 25–26 use substrates comprising HMT and various acetylindanes and show that these acetylindanes may be used instead of the corresponding indanes.

Example 27 uses a reversed order of addition, with crude HMT added to the other reagents.

Pure HMT substrate

Example 1

A 250 ml reactor was equipped with a mechanical stirrer, thermometer, addition funnel, an N$_2$ inlet and a double surface water condenser. The latter was fitted with a gas outlet leading to a gas scrubber. The reactor was charged with dry cyclohexane (25 g), HMT (25 g) and, after cooling to 20° C., acetyl chloride (11.55 g). The temperature of the resulting liquid was adjusted to 20° C. Aluminium chloride (18 g) was then added portionwise over 95 minutes keeping the reactor temperature at 20° C. The reaction mixture solidified after 82% of the aluminium chloride had been added. It became mobile and homogeneous after heating to 44° C.; the addition was then completed at this elevated temperature.

The reactor contents were quenched by the dropwise addition of water (50 g) and the resulting two phases were stirred for 0.5 hrs. After settling, the mixture was separated, and the organic phase washed with 25 g sodium hydroxide solution (10% w/w) and twice with 25 g water. The cyclohexane solvent was removed from the crude product under reduced pressure on a rotary evaporator.

The yield of acetyl-HMT in the crude product (by standardised glc; internal standard analysis) was 91.4%.

Although this Example appears to give acceptable results, such processing of pure HMT is not reliably repeatable in a predictable manner, as evidenced by the following Examples 1a to 1f, and so is not suitable as the basis for a commercial process.

Example 1a

The method of Example 1 was repeated. The mixture solidified after 54% of the aluminium chloride had been added. The mixture became mobile at 44°–46° C. The yield of acetyl-HMT in the crude product (by standardised glc; internal standard analysis) was 91.4%.

Example 1b

The method of Example 1 was followed except the quantities used were HMT (50 g), acetyl chloride (23 g), cyclohexane (50 g) and aluminium chloride (18 g); in addition the experiment was conducted at 40° C. The mixture solidified after 50% of the aluminium chloride had been added. The mixture became mobile at 65° C. The yield of acetyl-HMT in the crude product was 80.3%, based on converted HMT. HMT not converted was recovered.

Example 1c

The method of Example 1b was followed except the temperature was increased from 30° to 50° C. during the addition. The mixture remained mobile. The yield of acetyl-HMT in the crude product was 69.2%.

Example 1d

The method of Example 1c was repeated. The mixture remained mobile.

The yield acetyl-HMT in the crude product was 87%.

Example 1e

The method of Example 1c was repeated. The mixture remained mobile.

The yield of acetyl-HMT in the crude product was 70.6%.

Example 1f

The method of Example 1c was repeated on a 33% larger scale. The mixture solidified after 50% of the aluminium chloride had been added. It became mobile at 60° C. The yield of acetyl-HMT in the crude product was 80.6%.

Similar results (not shown) to those given above are obtained when reacting pure HMT in the presence of other solvents such as trans decalin, methylcyclohexane, 2,2,4-trimethylpentane and n-pentane.

Crude HMT Substrate

Example 2

A 250 ml reactor was equipped with a mechanical stirrer, thermometer, addition funnel, an $N_2$ inlet and a double surface water condenser. The latter was fitted with a gas outlet leading to a gas scrubber. The reactor was charged with dry cyclohexane (25 g), crude HMT (25 g) and, after cooling to 20° C., acetyl chloride (11.55 g). The composition of the crude HMT is given below. The temperature of the resulting liquid was adjusted to 20° C. Aluminium chloride (18 g) was then added portionwise over 95 minutes keeping the reactor temperature at 20° C. The reaction mixture remained liquid until the completion of the addition, and for a further 2.5 hrs post addition stir. The reactor contents were quenched by pouring into water (50 g) and the resulting two phases were stirred for 0.5 hrs. After settling, the mixture was separated, and the organic phase washed with sodium hydroxide (10%w/w) solution (25 g) and twice with water (2×25 g). The cyclohexane solvent was removed from the crude product under reduced pressure on a rotary evaporator.

The yield of acetyl-HMT in the crude product was 85.6%.

The crude HMT had the following composition:
HMT: 74.7%
1-isopropyl-1,3,3,6-tetramethylindane (ITMI): 14.0%
1-(4-methylphenyl)-1,3,3,6-tetramethylindane (MPTMI):5.8%
The balance was made up of p-cymene 1.5%
The crude HMT was obtained as follows:

p-Cymene (500 ml) was charged to a 2 liter vessel equipped with a stirrer, a thermometer, a nitrogen inlet, a reflux condenser and two addition ports. The solvent was cooled to −20° C. and thereafter a mixture of 150 g p-cymenol and 130 g 2,3-dimethylbut-1-ene was added through one port and simultaneously 55 ml of titanium tetrachloride was added through the other port while stirring. The flows were regulated such that both aditions took 1.5 hours. During the additions, the temperature was maintained at −20° C. After the addition, the reaction mixture was stirred for another 10 minutes, quenched into 500 ml water and the. resulting mixture stirred for 30 minutes. The organic phase was separated and washed successively with 10% v/v hydrochloric acid solution (200 ml), 10% w/w sodium hydroxide solution (200 ml) and water (300 ml).

The solvent was removed by distillation to yield a crude product comprising 146.1 g HMT (71.9% yield) in addition to 42.9 g ITMI and some minor products, including about 8.9 g of MPTMI.

Example 3

The method of Example 2 was followed except the reaction was carried out at 10° C., and post addition stirring was continued for 1 hour.

The yield of acetyl-HMT (by standardised glc; internal standard analysis) was 95.5%.

Example 4

The method of Example 2 was followed except the solvent employed was trans decalin. The reaction mixture remained mobile.

The yield of acetyl-HMT in the crude product was 94%.

Example 5

The method of Example 2 was followed except the solvent employed was methylcylohexane. The reaction mixture remained mobile.

The yield of acetyl-HMT in the crude product was 95.2%.

Example 6

The method of Example 2 was followed except the solvent was 2,2,4-trimethylpentane. The mixture solidified after 92% of the aluminium chloride had been added. The mixture became mobile at 55°–60° C.; two distinct phases formed in the reactor.

The yield of acetyl-HMT in the crude product was 77.6%.

Example 7

The method of Example 2 was followed except the solvent employed was n-pentane. The mixture solidified after 80% of the aluminium chloride had been added. On heating, the mixture became mobile at 37° C.

The yield of acetyl-HMT in the crude product was 84.5%.

HMT+substituted indane substrate

Example 8

The method of Example 1 was followed except that the substrate employed comprised ITMI 99.3% and HMT 0.3%. The mixture solidified after 100% of the aluminium chloride had been added. On heating, the mixture became mobile at 80° C.

The yield of acetyl-HMT in the crude product (by glc; relative peak area) was 90.7%.

Example 9

The method of Example 1 was followed except that the substrate employed comprised ITMI 50% and HMT 50%. The mixture solidified after 100% of the aluminium chloride had been added. On heating, the mixture became mobile at 47° C. The mixture was stirred for 20 minutes.

The yield of acetyl-HMT in the crude product (by standarised glc; internal standard analysis) was 91.4%.

Example 10

The method of Example 1 was followed except that the substrate employed comprised ITMI 40% and HMT 60%. The mixture solidified after 100% of the aluminium chloride had been added. On heating, the mixture became mobile at 32° C.

The yield of acetyl-HMT in the crude product was 90.9%.

Example 11

The method of Example 1 was followed except that the substrate employed comprised ITMI 34.9% and HMT 63.8%. The mixture solidified after 100% of the aluminium chloride had been added. On heating, the mixture became mobile at 32° C. The mixture was stirred for 15 mins. The yield of acetyl-HMT in the crude product was 93.7%.

Example 12

The method of Example 1 was followed except that the substrate employed comprised ITMI 29.7% and HMT 69.2%. The mixture solidified after 100% of the aluminium chloride had been added. On heating, the mixture became mobile at 37° C.

The yield of acetyl-HMT in the crude product was 96.8%.

Example 13

The method of Example 1 was followed except that the substrate employed comprised ITMI 20.1% and HMT 79.1%. The mixture solidified after 97% of the aluminium chloride had been added. On heating, the mixture became mobile at 34° C.

The yield of acetyl-HMT in the crude product was 96.3%.

Example 14

The method of Example 1 was followed except that the substrate employed comprised ITMI 30% and HMT 70%. the mixture solidified after 100% of the aluminium chloride had been added. On heating, the mixture became mobile at 37° C.

The yield of acetyl-HMT in the crude product was 96.8%.

Example 15

The method of Example 1 was followed except that the substrate employed comprised 1,1,2,3,3,6-hexamethylindane 29.4%, 1-ethyl-1,3,3,6-tetramethylindane 1.8% and HMT 68.6%. The mixture solidified after 100% of the aluminium chloride had been added. On heating, the mixture became mobile at 39° C. The mixture was stirred for 40 minutes. The yield of acetyl-HMT in the crude product was 87.3%.

Example 16

The method of Example 1 was followed except that the substrate employed comprised 1-isopropyl-2,3,3,5-tetramethylindane 29.4%, small quantities of isomeric indanes and HMT 68.4%. The mixture solidified after 100% of the aluminium chloride had been added. On heating, the mixture became mobile at 35° C. The mixture was stirred for 120 minutes.

The yield of acetyl-HMT in the crude product was 98%.

Example 17

Figure 4:
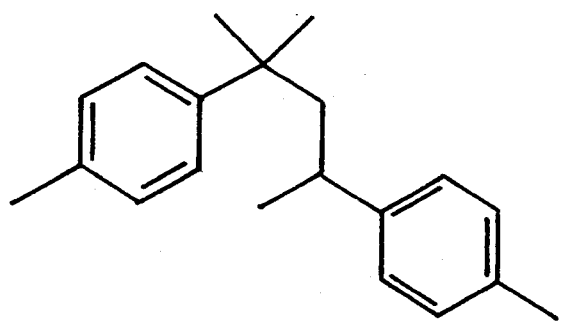
FIG. 4 shows the structure of a cymene dimer.

The method of Example 1 was followed except that the substrate employed comprised MPTMI 31.4% and HMT 66.9%. The mixture contained a trace of a cymene dimer, the structure of which is shown in FIG. 4. The mixture did not solidify after 100% of the aluminium chloride had been added, and the mixture was stirred for 210 minutes.

The yield of acetyl-HMT in the crude product was 87%.

Example 18

The method of Example 1 was followed except that the substrate employed comprised MPTMI 7.6% and HMT 92.1%. The mixture contained a trace of the cymene dimer of FIG. 4. The mixture solidified after 100% of the aluminium chloride had been added. On heating, the mixture became mobile at 53° C. The mixture was stirred for 40 minutes.

The yield of acetyl-HMT in the crude product was 87.6%.

Example 19

The method of Example 1 was followed except that the substrate employed comprised MPTMI 15.0% and HMT 83.9%. The mixture contained 1.1% of the cymene dimer of FIG. 4. The mixture did not solidify after 100% of the aluminium chloride had been added, and the mixture was stirred for 150 minutes.

The yield of acetyl-HMT in the crude product was 85.3%.

Example 20

The method of Example 1 was followed except that the substrate comprised MPTMI 22.4% and HMT 76.4%. The mixture contained 1.7% of the cymene dimer of FIG. 4. The mixture solidified after 100% of the aluminium chloride had been added. On heating, the mixture became mobile at 29° C. The mixture was stirred for 60 minutes.

The yield of acetyl-HMT in the crude product was 84.9%.

Example 21

A 250 ml reactor was equipped with a mechanical stirrer, thermometer, addition funnel, an $N_2$ inlet and a double surface water condenser. The latter was fitted with a gas outlet to a gas scrubber. The reactor was charged with dry cyclohexane (25 g), a mixture of MPTMI 45.7% and HMT 46.8% (total 25 g) and, after cooling to 20° C., acetyl chloride (12.64 g). The MPTMI/HMT mixture contained 4.2% of the cymene dimer of FIG. 4; a slight excess of acetylating power was used to allow for the extra aromatic ring in the indane molecule. The temperature of the resulting liquid was adjusted to 20° C. Aluminium chloride (19.9 g) was then added portionwise over 95 minutes keeping the reactor temperature at 20° C. The mixture did not solidify after 100% of the aluminium chloride had been added, and the mixture was stirred for 240 minutes.

The reactor contents were quenched by the dropwise addition of water (50 g) and the resulting two phases were stirred for 0.5 hrs. After settling, the mixture was separated, and the organic phase washed with sodium hydroxide (10%w/w) solution (25 g) and twice with water (2×25 g). The cyclohexane solvent was removed from the crude product under reduced pressure on a rotary evaporator.

The yield of acetyl-HMT in the crude product was 82.2%.

Ternary Substrate

Example 22

The method of Example 1 was followed except that the substrate employed comprised ITMI 28.7%, MPTMI 5.0% and HMT 66.3%. The mixture solidified after 100% of the aluminium chloride had been added, but on heating the mixture became mobile at 35° C. Stirring was continued for 180 mins.

The yield of acetyl-HMT in the crude product was 92%.

Example 23

The method of Example 1 was followed except that the substrate employed comprised ITMI 27.7%, MPTMI 7.7% and HMT 64.6%. The mixture did not solidify even after minutes stirring.

The yield of acetyl-HMT in the crude product was 90.4%.

Example 24

The method of Example 1 was followed except that the substrate employed comprised ITMI 27.0%, MPTMI 10.0% and HMT 63.0%. The mixture did not solidify even after 270 minutes stirring.

The yield of acetyl-HMT in the crude product was 86%.

HMT+Acetylindane Substrate

Example 25

The method of Example 12 was followed except that the substrate employed comprised 5-acetyl-1-isopropyl-1,3,3,6-tetramethylindane (5-acetyl-ITMI) 33.8% and HMT 66.2%. In this Example, the quantity of acetyl chloride was reduced by an equivalent to the number of moles of acetyl derivative present. This was to allow for acetyl chloride not being consumed by the additive and thus to approximate to similar solvent polarity at the end of the reaction. The mixture solidified after 95% of the aluminium chloride had been added. The mixture readily became mobile at 32° C. The yield of acetyl-HMT in the crude product was 89.6%.

Example 26

The method of Example 17 was followed except that the substrate employed comprised 5-acetyl-1-(4-methylphenyl)-1,3,3,6-tetramethylindane (5-acetyl-MPTMI) 33.1% and HMT 66.9%. The 5-acetyl-MPTMI was minimum 90% pure of the given isomer. The mixture remained mobile.

The yield of HMT in the crude product was 96.8%.

In Examples 25 and 26 the quantities of acetyl additive employed result in the same mole ratio of indane to tetralin moiety as used in the non-acetylated additive Examples.

Reversed Addition

Example 27

A 3000 ml reactor was equipped with a mechanical stirrer, thermometer, equilibrated addition funnel, an $N_2$ inlet and a double surface water condenser. The latter was fitted with a gas outlet leading to a gas scrubber. The reactor was charged with aluminium chloride (333.3 g) and dry cyclohexane (264 g). The resulting slurry was cooled to 5° C. and stirred while acetyl chloride (215.9 g) was added over 55 mins, maintaining the temperature below 15° C. Crude HMT as used in the Example 2 (530 g) in cyclohexane (270 g) was added over 90 minutes keeping the temperature at 10° C. Stirring was continued for a further 30 minutes. The quench, work up and solvent removal procedure of Example 1 was scaled up pro rata and applied to the reaction mixture to yield the crude product.

The yield of acetyl-HMT in the crude product was 98.4%.

We claim:

1. A method of acylating 1,2,3,4-tetrahydro-1,1,2,4,4,7-hexamethylnapthalene (HMT) to produce 6-acyl-1,2,3,4-tetrahydro-1,1,2,4,4,7-hexamethylnapthalene (acyl-HMT), comprising subjecting a mixture of 1,2,3,4-tetrahydro-1,1,2,4,4,7-hexamethylnapthalene in an amount of about 60 to 85% by weight and one or more indanes selected from the group consisting of substituted indanes having up to 20 carbon atoms and the corresponding substituted acylindanes to a Friedel-Crafts acylation reaction at a temperature below about 40° C., in the presence of a saturated nonhalogenated hydrocarbon solvent wherein the weight ratio of solvent to HMT and indanes is 10:1 or lower, the indane functioning to prevent solidification of the acylation reaction mixture which would otherwise occur by acylating HMT in the presence of said hydrocarbon solvent.

2. A method according to claim 1, wherein the substituted indane is selected from the group consisting of 1-isopropyl,-1,3,3,6-tetramethylindane (ITMI), 1-(4-methylphenyl)-1,3,3,6-tetramethylindane (MPTMI), 1,1,2,3,3,6-hexamethylindane, 1-ethyl-1,3,3,6-tetramethylindane, and 1-isopropyl-2,3,3,5-tetramethylindane and/or the corresponding acyl-indane.

3. A method according to claim 1 wherein acylindane produced in the method is recycled.

4. A method according to claim 2, using a mixture of ITMI and MPTMI, together constituting between 15 and 40% by weight of the total reaction mixture.

5. A method according to claim 4 using the following mixture:
HMT: 65 to 80% by weight
ITMI: 10 to 25% by weight
MPTMI: 2 to 25% by weight.

6. A method according to claim 5 wherein the mixture is obtained by Friedel-Crafts alkylation of p-cymen-8-ol with a suitable alkene to give HMT, with MPTMI and ITMI as byproducts.

7. A method according to claim 1, wherein the hydrocarbon solvent is alicyclic.

8. A method according to claim 1, wherein the Lewis acid catalyst is aluminium chloride.

9. A method according to claim 1, wherein the acylation reaction is carried out using an acetylation reagent.

10. A method according to claim 9 wherein the acetylating reagent is present in up to 20% molar excess.

11. A composition of matter comprising a mixture of 6-acetyl-1,2,3,4,-tetrahydro-1,1,2,4,4,7-hexamethyl napthalene in an amount in the range 60 to 90%, and one or more acetyl-indane(s) selected from 1-ispropyl,-1,3,3,6-tetramethylindane (ITMI), 1-(4-methylphenyl),-1,3,3,6-tetramethylindane (MPTMI), 1,1,2,3,3,6-hexamethylindane. 1-ethyl-1,3,3,6-tetramethylindane, and 1-isopropyl-2,3,3,5-tetramethylindane and/or the corresponding acyl-indane in an amount in the range 10 to 40%, preferably 15–40% by weight.

12. A composition of matter according to claim 11 comprising a mixture obtained by Friedel Crafts acetylation of a mixture comprising 65–80% by weight of HMT, 10–25% by weight of ITM and 2–25% by weight of MPTMI in the presence of a non-halogenated saturated hydrocarbon solvent.

13. In the process for acetytating 1,2,3,4-tetrahydro-1,1,2,4,4,7-hexamethylnapthalene (HMT) to produce 6-acetyl-1,2,3,4-tetrahydro-1,1,2,4,4,7-hexamethylnapthalene (acyl-HMT) the improvement comprising subjecting HMT to a Friedel-Crafts acetylation reaction in the presence of a non-halogenated saturated hydrocarbon solvent and at least one compound selected from the group consisting of substituted indanes of up to 20 carbon atoms and the corresponding acyl indanes, the said compound functioning to prevent solidification of the reaction mixture.

14. Perfumes comprising the acylated product produced by the method according to any one of claims 1, 2, 3, 4, 7, 8, 10 and 13.

15. The method of claim 1 wherein the acylation reaction is carried out at a temperature below about 25° C. and the ratio of solvent to HMT is 5:1 or lower.

16. The method of claim 1 wherein the solvent is selected from the group consisting of cyclohexane, methylcyclohexane and trans-decalin.

17. The method of claim 9 wherein the acetylation reagent is acetyl halogenide.

* * * * *